United States Patent [19]

Sone et al.

[11] Patent Number: 5,434,116
[45] Date of Patent: Jul. 18, 1995

[54] ORGANIC TRANSITION METAL COMPOUND HAVING π-BONDING HETEROCYCLIC LIGAND AND METHOD OF POLYMERIZING OLEFIN BY USING THE SAME

[75] Inventors: Makoto Sone, Mie; Akihiro Yano, Yokkaichi, both of Japan

[73] Assignee: Tosoh Corporation, Shinnanyo, Japan

[21] Appl. No.: 70,286

[22] Filed: Jun. 2, 1993

[30] Foreign Application Priority Data

Jun. 5, 1992 [JP] Japan .................................. 4-169897
Aug. 12, 1992 [JP] Japan .................................. 4-235118
Oct. 30, 1992 [JP] Japan .................................. 4-293198

[51] Int. Cl.$^6$ .......................... B01J 31/00; C08F 4/60; C07F 19/00
[52] U.S. Cl. .................................. 502/103; 502/117; 502/118; 502/152; 548/402; 548/404; 556/12; 556/14; 556/20; 556/22; 556/23; 556/28; 556/43; 556/46; 556/52; 556/1
[58] Field of Search ........................ 556/12, 14, 20, 22, 556/23, 28, 43, 46, 52, 1; 548/402, 404; 534/15; 502/103, 117, 118, 152

[56] References Cited

FOREIGN PATENT DOCUMENTS 0053987 6/1982 European Pat. Off. .
0283739 9/1988 European Pat. Off. .
0420436 4/1991 European Pat. Off. .
0423101 4/1991 European Pat. Off. .

OTHER PUBLICATIONS

Chemical Abstracts, vol. 110, 1989, AN-231796v, F. Nief, et al., "Synthesis of Phospha- and Diphosphatitanocene Dichlorides. Crystal and Molecular Structures of Bis(.η.5-3,4 Dimethylphospholyl)Dichlorotitanium(IV) and of (.η.5-3,4-Dimethylphospholyl)Trichlorotitanium(IV)".
Journal of Organometallic Chemistry, vol. 193, 1980, pp. C13-C16, P. Meunier, et al, "Synthesis of Phospha- and Diphospha-Zirconocene Dichlorides".
Journal of the Chemical Society, Chemical Communications 1988, pp. 770–771, F. Nief, et al., "1-Trimethylstannylphospholes as Precursors of .η.5-Phospholyl Complexes. Synthesis of (.η.5-Phospholyl)Trichlorotitanium(IV) Complexes".
Journal of Organometallic Chemistry, vol. 384, pp. 271–278, F. Nief, et al., "Reactivity of a Diphosphazirconocene Dichloride, (.η.5-C4ME4P)2ZRCL2. Crystal and Molecular Structure of a Metal-Bridged Bis(.-π.-Heterocyclopentadienyl) Zirconium Complex, (CO) 3FE(.μ.-.η.5,.η.-1-C4ME4P)2ZRCL2" 1990.

*Primary Examiner*—Porfirio Nazario Gonzalez
*Attorney, Agent, or Firm*—Oblon, Spivak, McClelland, Maier & Neustadt

[57] ABSTRACT

A transition metal organometallic compound comprising a transition metal in any one of group 3A to group 8 of the periodic table and cyclic compounds containing a heteroaom in group 5 or group 5B of the periodic table and having a cyclic structure including a π-bonded portion and composed of said heteroatom and said π-bonded portion, wherein said transition metal has a bond of a π-binding heterocylic ligand, said heteroatom and said π-bonded portion and a catalyst for polymerizing olefin comprising the above organic metal compound and an organic compound.

5 Claims, 4 Drawing Sheets

ORGANIC TRANSITION METAL COMPOUND HAVING π-BONDING HETEROCYCLIC LIGAND AND METHOD OF POLYMERIZING OLEFIN BY USING THE SAME

BACKGROUND OF THE INVENTION

1. Field of the Invention

This invention relates to a transition metal organometallic compound comprising a transition metal in any one of group 3 to group 10 of the periodic table and cyclic compounds containing a heteroatom in group 15 or of the periodic table and having a cyclic structure including a π-bonded portion and composed of the heteroatom and the π-bonded portion, wherein the transition metal has a bond of a π-bonding heterocyclic ligand, the heteroatom and the π-bonded portion, relates to a catalyst system using the foregoing transition metal organometallic compound as a main catalyst and using solely an organometallic compound, aluminoxane or ionized ionic compound or their combinations as a co-catalyst, and relates to a method of polymerizing olefin in the presence of the foregoing catalyst.

2. Description of the Related Art

A variety of polymerization methods and catalyzer systems have been known for use to polymerize olefin. It has been known that a conventional Ziegler-Natta catalyst composed of a transition metal compound using alkyl aluminum as a co-catalyst is able to manufacture Polyolefin that exhibits a wide distribution of molecular weight.

Recently, a catalyst system including a transition metal compound (generally called a "metallocene compound") that contains a cyclopentadienyl derivative as a ligand has been developed. The foregoing catalyst system serves as a polymerizing catalyst for olefin, and, in particular, metallocene composed of group IVA transition metal such as titanium, zirconium or hafnium has been used to manufacture polyethylene, ethylene copolymer or polypropylene or the like. It has been found that use of aluminoxane as a co-catalyst enables polyolefin to be manufactured actively (for example, see Japanese Patent Laid-Open No. 58-19309).

A multiplicity of investigations have been made and results have been reported about catalyst systems of the type containing a group IVA metallocene compound and aluminoxane, the group IVA metallocene compound having a variety of cyclopentadienyl derivatives. As a result, it has been found that introduction of a variety of substituents into the cyclopentadienyl group enables the stereostructure of generated polymer, the primary structure such as the composition distribution and the manufacturing efficiency to be controlled (for example, see Japanese Patent Laid-Open No. 61-26491, Japanese Patent Laid-Open No. 64-51408, Japanese Patent Laid-Open No. 64-66216, Japanese Patent Laid-Open No. 1-301704 and J. Am. Chem. Soc. 1988, 110, 6255-62 and so forth).

Since a necessity of using a large quantity of aluminoxane raises an industrial problem, investigations have been undertaken to use a variety of organic metal compounds to serve as a co-catalyst in place of aluminoxane (for example, see Japanese Patent Laid-Open No. 3-197513, Japanese Patent Laid-Open No. 3-290408 and so forth) and investigations of polymerization of olefin using cationic metallocene compound (for example, see Japanese Patent Laid-Open No. 3-207704 and so forth) have been undertaken.

According to the foregoing specifications, polymer obtainable from the polymerization using the metallocene compound exhibits several characteristics that the quantity of oligomer that raises a problem in terms of performing a process is small and that a uniform composition distribution is attained when it is used to manufacture polypropylene or ethylene-α-olefin copolymer. However, its narrow molecular weight distribution raises problems in terms of the processability and mechanical strength. Although a variety of investigations have been undertaken to overcome the foregoing problems, a satisfactory result has not been obtained yet. Accordingly, there arises a necessity of developing a novel catalyst system that is able to overcome the foregoing problems.

SUMMARY OF THE INVENTION

This invention aims to solve the foregoing problems.

It is, therefore, an object of this invention is to provide a catalyst that is capable of efficiently manufacturing polyolefin exhibiting excellent physical properties and processability and to provide a method of polymerizing olefin by using the catalyst.

DETAILED DESCRIPTION OF THE PREFERRED EMBODIMENTS

A cyclopentadienyl group has a five-member cyclic structure of carbon and it has been used widely in an organometallic compounds as a ligand for stabilizing transition metal. Recently, a cyclic compound containing heteroatoms was reported in which a portion of five carbons of the cyclopentadienyl group is substituted by a heteroatom such as phosphorus or sulfur to have a structure similar to that of the cyclopentadienyl group but to have different characteristics. A group including F.Massie has reported some transition metal compounds of a type containing a phosphoryl group having a five-member cyclic structure which is similar to that of the cyclopentadienyl group. In Organometallics, 1988, 7, 921, a group IVA transition metal compound having a phosphoryl group was reported. Further, a report was made in J.Organomet. Chemistry, 1990, 384, 271 that a reaction of the foregoing compound and an iron carbonyl compound generates a polynucleus transition metal compound of iron-zirconium in which iron cross-links two phosphoryl groups.

As a result of studies performed by the inventors of this invention, it has been found that sole use of a transition metal organometallic compound comprising a transition metal in any one of group 3 to group 10 of the periodic table and cyclic compounds containing a heteroatom in group 15 of the periodic table and having a cyclic structure including a π-bonded portion and com- posed of the heteroatom and the π-bonded portion, wherein the transition metal has a bond of a π-bonding heterocyclic ligand, the heteroatom and the π-bonded portion, or an organic metal compound, or aluminoxane or ionized ionic compound or combination of them to coexist enables polymerizing activity with respect to olefin to be attained. Thus, the present invention was found.

According to the present invention, there is provided a transition metal organometallic compound comprising a transition metal in any one of group 3 to group 10 of the periodic table and cyclic compounds containing a heteroatom in group 15 of the periodic table and having a cyclic structure including a π-bonded portion and composed of the heteroatom and the π-bonded portion, wherein the transition metal has a bond of a π-bonding heterocyclic ligand, the heteroatom and the π-bonded portion.

According to the present invention, there is provided a transition metal organometallic compound according to claim 1, wherein the structure of the compound is expressed by the following general formula (1):

(1)

where A and B respectively are expressed by general formulas (2) and (3):

where E and E' respectively are heteroatoms in group 15 of the periodic table, $R^1$, $R^2$, $R^3$, $R^4$, $R^5$, $R^6$, $R^7$ and $R^8$ may be the same or different from one another, $R^1$, $R^2$, $R^3$, $R^4$, $R^5$, $R^6$, $R^7$ and $R^8$ being hydrogen, or a hydrocarbon group such as an alkyl group, an aryl group or an aralkyl group, or an acyl group, a cyanide group, a silyl group or a germyl group, $M^1$ is transition metal in any one of group 3 to group 10 of the periodic table, and X may be the same or different from one another, X being hydrogen, alkyl group, aryl group, aralkyl group, acyl group, cyanide group, silyl group, germyl group, amide group, azide group, phosphide group, alkoxide group, aryloxide, silyloxide, sulfide, or halogen, and n is an integer from 1 to 4.

According to the present invention, there is provided a transition metal organometallic compound according to claim 1, wherein the structure of the compound is expressed by the following general formula (4):

(4)

where A, B, E, E', $R^1$ to $R^8$, $M^1$, X and n denote the same contents as those described above, $M^2$ is transition metal in any one of group 3 to group 10 of the periodic table or a typical element (carbon and silicon excluded) in any one of groups 1, 2, 13 and 14, $M^2$ being bonded to A and/or B with the heteroatoms (E and E'), L may be the same or different from one another, L being a ligand, organic metal compound, transition metal compound and salt for stabilizing the transition metal $M^2$, and m is an integer larger than zero.

According to the present invention, there is provided a transition metal organometallic compound according to claim 1, wherein the structure of the compound is expressed by the following general formula (5):

(5)

where A, E, $R^1$ to $R^4$, $M^1$, X and n denote the same contents as those described above, and $R^9$ is a cyclopentadienyl group or a substituted cyclopentadienyl group. Further, the present invention relates to a catalyst for polymerizing olefin having, as the components, the foregoing transition metal organometallic compound and an organometallic compound, and to a method of polymerizing olefin that uses the same.

DETAILED DESCRIPTION OF THE PREFERRED EMBODIMENTS

The present invention will now be described in detail.

The transition metal organometallic compound that is the component of the catalyst for use in the present invention is a transition metal organometallic compound comprising a transition metal in any one of group 3 to group 10 of the periodic table and cyclic compounds containing a heteroatom in group 15 of the periodic table and having a cyclic structure including a π-bonded portion and composed of the heteroatom and the π-bonded portion, wherein the transition metal has a bond of a π-bonding heterocyclic ligand, the heteroatom and the π-bonded portion, the transition metal organometallic compound being expressed by general formula (1), general formula (4) or general formula (5).

The foregoing transition metal organometallic compound has the π-bonding heterocyclic ligand expressed by general formula (2) and (3), E and E' has a heteroatom in group 15, preferably nitrogen, phosphorus, arsenic or antimony, and most preferably nitrogen or phosphorus.

$R^1$ to $R^8$ may be the same or different from one another, $R^1$ to $R^8$ being hydrogen, or a hydrocarbon group such as an alkyl group, an aryl group or an aralkyl group, or an acyl group, a cyanide group, a silyl group or a germyl group. The siryl group is exemplified by a trimethylsilyl group, a triethylsilyl group, a butylsilyl group, a phenylsilyl group, a diphenylsilyl group and a triphenylsilyl group. The hydrocarbon group is exemplified by a methyl group, an ethyl group, a propyl group, a butyl group, a hexyl group, an octyl group, a phenyl group, a tolyl group, a cyclohexyl group and a benzil group.

Further, compounds having a cyclic carbon skeleton expressed by chemical formulas 5 to 14, for example, a phosphaindenyl group and a phosphafluorenyl group may be exemplified as the ligand.

Chemical Formula 5

Chemical Formula 6

Chemical Formula 7

Chemical Formula 8

Chemical Formula 9

Chemical Formula 10

Chemical Formula 11

-continued

Chemical Formula 12

Chemical Formula 13

Chemical Formula 14 where E and E' are heteroatoms in group 15, and R' and R" respectively are hydrogen a silyl group, or a hydrocarbon group such as an alkyl group, an aryl group or an aralkyl group.

The π-bonding heterocyclic ligand is bonded to the transition metal with the heteroatom or in the π-bonded portion to stabilize the foregoing transition metal organometallic compound.

The transition metal organometalic compound expressed by general formula (4) is composed of the transition metal $M^1$ and $M^2$, which is a typical element in any one of groups 1, 2, 13 and 14 (carbon and silicon excluded) of the periodic table or transition metal in any one of groups 3 to 10, $M^2$ being bonded to A and/or B in general formula (4) with the heteroatoms (E and E'). It is preferable that $M^2$ is magnesium, boron, aluminum, gallium, germanium, tin, scandium, titanium, zirconium, hafnium, vanadium, niobium, thallium, chromium, molybdenum, tungsten, manganese, technetium, rhenium, iron, ruthenium, osmium, cobalt, rhodium, iridium, nickel, palladium or platinum.

The ligand L for stabilizing $M^2$ is a Lewis base of a unsaturated hydrocarbon group or the like typified by: carbonyl, phosphine, amine and ethylene; a hydride, halogen, cyanide, isocyanide, alkoxide, amide, phosphide, and a hydrocarbon group such as an alkyl group, an aryl group, or an aralkyl group or a cycloalkadienyl group, an organometallic compound and a transition metal compound. Symbol m is an integer larger than 0.

The ligand L is specifically exemplified by oxygen, ether, tetrahydrofuran, phosphorus, phosphine, phenylphosphine, methylphosphine, diphenylphosphine, dimethylphosphine, triphenylphosphine, trimethylphosphine, bis(diphenylphosphino)ethane, bis(diphenylphosphino)butane, bis(dimethylphosphino)ethane, and bis(dimethylphosphino)butane of a type that two or more phosphorus atoms are cross-linked, nitrogen, amine, methylamine, dimethylamine, trimethylamine, aniline, methylaniline, dimethylaniline, ethylene diamine, bis(dimethylamino)ethane and bipyridine of a type that two or more nitrogen atoms are cross-linked, carbon, carbonyl, ethylene, butadiene, cyclooctadiene, cyclooctatetraene, hydride, fluorine, chlorine, bromine, iodine, cyanide, isocyanide, methoxy, ethoxy, butoxy, methylamide, ethylamide, propylamide, butylamide, dimethylamide, diethylamide, dipropylamide, dibutylamide, phosphide, methylphosphide, ethylphosphide, butylphosphide, methyl, ethyl, propyl, butyl, phenyl, tolyl, phenyl, aryl, benzyl, cycloalkadienyl such as cyclopentadienyl, substituted cyclopentadienyl, fluorenyl or indenyl, carbon dioxide, carbon disulfide, a cluster compound containing carborane or M1, for example, a manganese carbonyl compound, an iron carbonyl compound or a ruthenium carbonyl compound or inorganic salt. However, the present invention is not limited to the foregoing materials.

X may be the same or different from one another, X being hydrogen, an alkyl group, an aryl group, an aralkyl group, an acyl group, a cyanide group, a siryl group, a germyl group, an amide group, an azide group, a phosphide group, alkoxide, aryloxide, silyl oxide, sulfide, or halogen. Symbol n is an integer from 1 to 4.

X is exemplified by fluorine, chlorine, bromine, iodine, a trimethylsilyl group, a triethylsilyl group, a butylsilyl group, a phenylsilyl group, a trimethyl germyl group, a trietyl germyl-group, a butyl germyl group, a phenyl germyl group, a diphenylsilyl group, a triphenyl silyl group, a methyl group, an ethyl group, a propyl group, a butyl group, a hexyl group, an octyl group, a phenyl group, a tolyl group, a cyclohexyl group, a benzyl group, a methoxy group, an ethoxy group, a dimethyl amide group, a diethyl amide group, a dipropyl amide group, a dimethyl phosphide group and a methyl sulfide group.

The transition metal organometallic compound expressed by general formula (1) is specifically exemplified by bis(phosphoryl) scandium hydride, bis(phosphoryl)zirconium dimethyl, bis(phosphoryl) zirconium dichloride, bis(2-methylphosphoryl) scandium hydride, bis(2-methylphosphoryl) zirconium dimethyl, bis(2-methylphosphoryl) zirconium dichloride, bis(3-methylphosphoryl) scandium hydride, bis(3-methylphosphoryl) zirconium dimethyl, bis(3-methylphosphoryl) scandium dichloride, bis(2,3-dimethylphosphoryl) scandium hydride, bis(2,3-dimethylphosphoryl) zirconium dimethyl, bis(2,3-dimethylphosphoryl) zirconium dichloride, bis(2,4-dimethylphosphoryl) scandium hydride, bis(2,4-dimethylphosphoryl) zirconium dimethyl, bis(2,4-dimethylphosphoryl) zirconium dichloride, bis(2,5-dimethylphosphoryl) scandium hydride, bis(2,5-dimethylphosphoryl) zirconium dimethyl, bis(2,5-dimethylphosphoryl) zirconium dichloride, bis(3,4-dimethyl phosphoryl) scandium hydride, bis(3,4-dimethyl phosphoryl) zirconium dimethyl, bis(3,4-dimethylphosphoryl) zirconium dichloride, bis(2,3,4-trimethylphosphoryl) scandium hydride, bis(2,3,4-trimethylphosphoryl) scandium hydride, bis(2,3,4-trimethylphosphonyl) zirconium dimethyl, bis(2,3,4-trimethylphosphoryl) zirconium dichloride, bis(2,3,5-trimethylphosphoryl) scandium hydride, bis(2,3,5-trimethylphosphoryl) zirconium dimethyl, bis(2,3,5-trimethylphosphoryl) zirconium dichloride, bis(2,3,4,5-tetramethyl phosphoryl) scandium hydride, bis(2,3,4,5-tetramethyl phosphoryl) zirconium dimethyl, bis(2,3,4,5-tetramethyl phosphoryl) zirconium dichloride, bis(phosphaindenyl) zirconium dimethyl, bis(phosphafluorenyl) zirconium dichloride, (phosphoryl) (phosindenyl) zirconium dimethyl, (phosphoryl) (phosphaindenyl) zirconium dichloride, (2-methyl phosphoryl) (phosphaindenyl) zirconium dimethyl, (2-methyl phosphoryl) (phosphaindenyl) zirconium dichloride, (3-methyl phosphoryl) (phosphaindenyl) zirconium dimethyl, (3-methyl phosphoryl) (phosphaindenyl) zirconium dichloride, 2,3-dimethyl phosphoryl) (phosphaindenyl) zirconium dimethyl, (2,3-dimethyl phosphoryl) (phosphaindenyl) zirconium dichloride, (2,4-dimethyl phosphoryl) (phosphaindenyl) zirconium dimethyl, (2,4-dimethyl phosphoryl) (phosphaindenyl) zirconium dichloride, (2,5-dimethyl phosphoryl) (phosphaindenyl) zirconium dimethyl, (2,5-dimethyl phosphoryl) (phosphaindenyl) zirconium dichloride, (3,4-dimethyl phosphoryl) (phosphaindenyl) zirconium dimethyl, (3,4-dimethyl phosphoryl) (phosphaindenyl) zirconium dichloride, (2,3,4-trimethyl phosphoryl) (phosphaindenyl) zirconium dimethyl, (2,3,4-trimethyl phosphoryl) (phosphaindenyl) zirconium dichloride, (2,3,5-trimethyl phosphoryl) (phosphaindenyl) zirconium dimethyl, (2,3,5-trimethyl phosphoryl) (phosphaindenyl) zirconium dichloride, (2,3,4,5-tetramethyl phosphoryl) (phosphaindenyl) zirconium dimethyl, (2,3,4,5-tetramethyl phosphoryl) (phosphaindenyl) zirconium dichloride, (phosphafluorenyl) (phosphaindenyl) zirconium dichloride, (phosphoryl) (phosphafluorenyl) zirconium dimethyl, (phosphoryl) (phosphafluorenyl) zirconium dichloride, (2-methyl phosphoryl) (phosphafluorenyl) zirconium dimethyl, (2-methyl phosphoryl) (phosphafluorenyl) zirconium dichloride, (3-methyl phosphoryl) (phosphafluorenyl) zirconium dimethyl, (3-methyl phosphoryl) (phosphafluorenyl) zirconium dichloride, (2,3-dimethyl phosphoryl) (phosphafluorenyl) zirconium dimethyl, (2,3-dimethyl phosphoryl) (phosphafluorenyl) zirconium dichloride, (2,4-dimethyl phosphoryl) (phosphafluorenyl) zirconium dimethyl, (2,4 -dimethyl phosphoryl ) (phosphafluorenyl) zirconium dichloride, (2,5-dimethyl phosphoryl) (phosphafluorenyl) zirconium dimethyl, (2,5-dimethyl phosphoryl) (phosphafluorenyl) zirconium dichloride, (3,4-dimethyl phosphoryl) (phosphafluorenyl) zirconium dimethyl, (3,4-dimethyl phosphoryl) (phosphafluorenyl) zirconium dichloride, (2,3,4-trimethyl phosphoryl) (phosphafluorenyl) zirconium dimethyl, (2,3,4-trimethyl phosphoryl) (phosphafluorenyl) zirconium dichloride, (2,3,5-trimethyl phosphoryl) (phosphafluorenyl) zirconium dimethyl, (2,3,5-trimethyl phosphoryl) (phosphafluorenyl) zirconium dichloride, (2,3,4,5-tetramethyl) phosphoryl) (phosphafluorenyl) zirconium dimethyl, (2,3,4,5-tetramethyl phosphoryl) (phosphafluorenyl) zirconium dichloride, (phosphaindenyl) (phosphafluorenyl) zirconium dimethyl, material using yttrium in place of scandium that is the transition metal, and material using titanium or hafnium in place of zirconium. However, the present invention is not limited to the foregoing materials.

The metal portion bonded with the heteroatom of the ligand A and/or B of the transition metal organometallic compound expressed by general formula (4), that is, the portion expressed by general formula (9)

$$L_mM^2 \qquad (9)$$

is specifically exemplified by tricarbonyl iron, tricarbonyl ruthenium, tricarbonyl osmium, cyclopentadienyl cobalt, cyclopentadienyl rhodium, cyclopentadienyl iridium, tetracarbonyl chromium, tetracarbonyl molybdenum, tetracarbonyl tungsten, aluminum chloride, magnesium chloride, alumina, titania, nickel chloride, palladium chloride, and platinum chloride. However, the present invention is not limited to the foregoing materials.

$R^9$ of the transition metal organometallic compound expressed by general formula (5) is a cyclopentadienyl group or a substituted cyclopentadienyl group exemplified by a cyclopentadienyl group, a methyl cyclopentadienyl group, a butyl cyclopentadienyl group, a pentamethyl cyclopentadienyl group, an indenyl group, and a fluorenyl group. The organic transition metal compound expressed by general formula (5) is specifically exemplified by (cyclopentadienyl) (phosphoryl) scandium hydride, (cyclopentadienyl) (phosphoryl) zirconium dimetyl, (cyclopentadienyl) (phosphoryl) zirconium dichloride, (cyclopentadienyl) (2-methyl phosphoryl) scandium hydride, (cyclopentadienyl) (2-methyl phosphoryl) zirconium dimetyl, (cyclopentadienyl) (2-methyl phosphoryl) zirconium dichloride, (cyclopentadienyl) (3-methyl phosphoryl) scandium hydride, (cyclopentadienyl) (3-methyl phosphoryl) zirconium dimetyl, (cyclopentadienyl) (3-methyl phosphoryl) zirconium dichloride, (cyclopentadienyl) (2,3-dimethyl phosphoryl) scandium hydride, (cyclopentadienyl) (2,3-dimethyl phosphoryl) zirconium dimetyl, (cyclopentadienyl) (2,3-dimethyl phosphoryl) zirconium dichloride, (cyclopentadienyl) (2,4-dimethyl phosphoryl) scandium hydride, (cyclopentadienyl) (2,4-dimethyl phosphoryl) zirconium dimetyl, (cyclopentadienyl) (2,4-dimethyl phosphoryl) zirconium dichloride, (cyclopentadienyl) (2,5-dimethyl phosphoryl) scandium hydride, (cyclopentadienyl) (2,5-dimethyl phosphoryl) zirconium dimetyl, (cyclopentadienyl) (2,5-dimethyl phosphoryl) zirconium dichloride, (cyclopentadienyl) (3,4-dimethyl phosphoryl) scandium hydride, (cyclopentadienyl) (3,4-dimethyl phosphoryl) zirconium dimetyl, (cyclopentadienyl) (3,4-dimethyl phosphoryl) zirconium dichloride, (cyclopentadienyl) (2,3,4-trimethyl phosphoryl) scandium hydride, (cyclopentadienyl) (2,3,4-trimethyl phosphoryl) zirconium dimetyl, (cyclopentadienyl) (2,3,4-trimethyl phosphoryl) zirconium dichloride, (cyclopentadienyl) (2,3,5-trimethyl phosphoryl) scandium hydride, (cyclopentadienyl) (2,3,5-trimethyl phosphoryl) zirconium dimetyl, (cyclopentadienyl) (2,3,5-trimethyl phosphoryl) zirconium dichloride, (cyclopentadienyl) (2,3,4,5-tetramethyl phosphoryl) scandium hydride, (cyclopentadienyl) (2,3,4,5-tetramethyl phosphoryl) zirconium dimetyl, (cyclopentadienyl) (2,3,4,5-tetramethyl phosphoryl) zirconium dichloride, (cyclopentadienyl) (phosphaindenyl) zirconium dimethyl, (cyclopentadienyl) (phosphafluorenyl) zirconium chloride, material using yttrium in place of scandium that is the transition metal of the foregoing transition metal organometallic compound, material using titanium or hafnium in place of zirconium, and an organic transition metal compound using a methyl cyclopentadienyl group, a butyl cyclopentadienyl group, a pentametyl cyclopentadienyl group, an indenyl group or a fluorenyl group in place of the cyclopentadienyl group that is $R^9$ of general formula (5). However, the present invention is not limited to the foregoing materials.

The organometallic compound that is used together with the transition metal organometallic compound is exemplified by material composed of metal atoms in group 1A, 2A, 2B or 3B of the periodic table and containing one or more alkyl group. It is preferable that they are composed of lithium, boron, aluminum, magnesium and zinc. They may be the same or different from one another. The organometallic compound is exemplified by a compound having a hydrocarbon group of a type bonded to metal with hydrogen or carbon, such as alkyl, aryl or aralkyl, and having a substituent bonded to the metal with oxygen, such as alkoxide or halogen, the compound having one or more alkyl groups.

The organometallic compounds may be selectively employed to meet the desire, such as obtaining the aimed physical properties of the polymer or controlling the polymerization at the time of manufacture. The organometallic compound for use in the present invention is exemplified by alkyl lithium such as methyl lithium or butyl lithium; alkylborane such as triethyl borane; alkyl aluminum such as trimethyl aluminum, triethyl aluminum or triisobutyl aluminum; alkyl aluminum halide such as dimethyl aluminum fluoride, dimethyl aluminum chloride, diethyl aluminum chloride or diisobutyl aluminum chloride; alkyl magnesium such as dibutyl magnesium or butylethyl magnesium; Grignard agent such as methyl magnesium, chloride, methyl magnesium bromide, butyl magnesium chloride and butyl magnesium bromide; and alkylzinc such as diethylzinc or diphenylzinc. However, the present invention is not limited to the foregoing materials.

The material having the bond between aluminum and oxygen, that is an example of the organic metal compound, is exemplified by aluminoxane expressed by general formula (6) or (7). $R^{10}$ may be the same or different from one another, $R^{10}$ being hydrogen, halogen, alkoxide or a hydrocarbon group. Specifically, it is exemplified by chlorine, bromine, iodine, a methoxy group, an ethoxy group, a propoxy group, a butoxy group, a phenoxy group, a methyl group, an ethyl group, a propyl group, a butyl group, a hexyl group, a phenyl group, a toryl group, and a cyclohexyl group and the like. Symbol q is an integer from 0 to 100.

The method for manufacturing the foregoing compounds may be one of known methods exemplified by (1) a method for making a reaction by adding trialkylaluminum to a suspension of hydrocarbon medium comprising a compound having adsorption water and salt (for example, magnesium sulfate hydrate, copper sulfate hydrate, and aluminum sulfate hydrate) containing crystal water; and (2) a method for allowing water to act directly on trialkyl aluminum in the hydrocarbon medium.

Any one of the foregoing organometallic compounds may be used solely or in the form of a combination consisting of two or more compounds to meet the object. It is preferable that the organometallic compound to be used solely is material containing aluminum, and more preferably aluminoxane. In the case where the two or more combined organometallic compounds are used, it is preferable that aluminoxane is contained as the component of the organic metal compound.

Although there is no limitation to a method of preparing the catalyst from the organometallic compound and the transition metal organometallic compound, a method is exemplified in which the preparation is performed in a solvent that is inert to the two compounds and another method is exemplified in which a monomer for the polymerization is mixed as a solvent. The temperature at which the foregoing process is performed in not limited particularly. Also the time period for the precess is not limited particularly.

The ratio of the transition metal organometallic compound and the organometallic compound to be set at the time of preparing the catalyst is not limited particularly. However, it is preferable that the mole ratio of the transition metal organometallic compound and the organometallic compound per metal atom is as follows:

(metal of transition metal organometallic
compound): (metal of the organometallic
compound)=100:1 to 1:1000000.

More preferably, the ratio is ranged from 1:1 to 100000.

The ionized ionic compound for use as the component of the catalyst according to the present invention is expressed by general formula (8):

$$[C^+][A^-] \qquad (8)$$

where [C⁺] is cation exemplified by: material containing active proton such as proton or Brønsted acid exemplified by trimethyl ammonium, triethylammonium, tripropylammonium, tributylammonium, N,N-dimethylanilinium, N,N-diethylanilinium, triphenylphosphonium, tri(o-tolyl)phosphonium or tri(p-tolyl) phosphonium and tri(mesityl)phosphonium carbonium, oxonium or sulfonium cation that does not contain active proton and that are exemplified by compounds such as triphenylcarbenium, tropylium ions, trimethyloxonium, triethyloxonium and triphenyloxonium; lithium ions, magnesium ions, palladium ions, platinum ions, copper ions, silver ions, gold ions, mercury ions and an etherate compound in which a base, such as, ether is coordinated in the foregoing ions; ferrocenium ions; and dimethylferrocenium ions. However, the present invention is not limited to this.

[A⁻] is anion which is not limited particularly and which is weakly coordinated with the foregoing transition metal compound. It is preferable to employ bulky and non-nucleophilic material which contains metal such as magnesium or aluminum having a charge or nonmetal such as halogen, boron or phosphorus, the material being a compound such as [AlR₄⁻], [BR₄⁻], [PR₆⁻] or [ClO₄⁻]. The material is exemplified by tetraphenylborate, tetra(pentafluorophenyl)borate, tetra(o-fluorophenyl)borate, tetra(p-fluorophenyl)borate, tetra(m-fluorophenyl)borate, tetra(3,5-difluorophenyl)borate, tetra(2,5-difluorophenyl)borate, tetra(2,6-difluorophenyl)borate, tetra(o-tolyl)borate, tetra(p-tolyl)borate, tetra(3,5-dimethylphenyl)borate, tetra(2,5-dimethylphenyl)borate, tetraphenylaluminate, tetra(pentafluorophenyl)aluminate, tetra(o-fluorophenyl)aluminate, tetra(p-fluorophenyl)aluminate, tetra(m-fluorophenyl)aluminate, tetra(3,5-difluorophenyl)aluminate, tetra(2,5-difluorophenyl)aluminate, tetra(2,6-difluorophenyl)aluminate, tetra(o-tolyl)aluminate, tetra(p-tolyl)aluminate, tetra(3,5-dimethylphenyl)aluminate, tetra(2,5-dimethylphenyl)aluminate, octadecarborate, dodecarborate, 1-carbaundecarborate and 1-carbadodecarborate.

The ionized ionic compound is exemplified by lithium tetrakispentafluorophenyl borate, anilinium tetrakispentafluorophenyl borate, triphenylcarbenium tetrakispentafluorophenyl borate, tropinium tetrakispentafluorophenyl borate, lithium tetrakispentafluorophenyl aluminate, anilinium tetrakispentafluorophenyl aluminate, triphenylcarbenium tetrakispentafluorophenyl aluminate and tropylium tetrakispentafluorophenyl aluminate. However, the present invention is not limited to the foregoing materials.

The organometallic compound is composed of group 1A, 2A, 2B or 3B metal atoms of the periodic table as described above, the organometallic compound having one or more alkyl group. It is preferable that the organometallic compound is composed of lithium, boron, aluminum, magnesium and zinc. The atoms for constituting the organometallic compound may be the same or difference from one another, the organometallic compound being exemplified by material that has a hydrocarbon group bonded to metal with hydrogen or carbon such as an alkyl, aryl or aralkyl and a substituent bonded to metal with oxygen such as alkoxide or halogen, the material having one or more alkyl group. The organometallic compound is exemplified by alkyl lithium such as methyl lithium or butyl lithium, alkyl borane such as triethyl borane, alkyl aluminum such as trimethyl aluminum, triethyl aluminum or triisobutyl aluminum, alkyl aluminum halide such as dimethyl aluminum fluoride, dimethyl aluminum chloride, diethyl aluminum chloride or diisobutyl aluminum chloride, alkyl aluminum hydride such as diethylaluminum hydride or diisobutyl aluminum hydride, alkyl magnesium such as dibutyl magnesium or butylethyl magnesium, a Grignard agent such as methyl magnesium chloride, methyl magnesium bromide, butyl magnesium chloride or butyl magnesium bromide, and alkyl zinc such as diethyl zinc or diphenyl zinc. However, the present invention is not limited to the foregoing materials. Aluminoxane may be employed as described above.

Although there is no limitation to a method of preparing the catalyst from the ionized ionic compound, the organic transition metal compound and the organometallic compound, a method is exemplified in which the preparation is performed in a solvent that is inert to each component and another method is exemplified in which a monomer for the polymerization is mixed as a solvent. The order of the reactions of the components is not limited particularly. The temperature at which the foregoing process is performed in not limited particularly. Also the time period for the precess is not limited particularly.

The ratio of the transition metal organometallic compound and the organometallic compound to be set at the time of preparing the catalyst is not limited particularly. However, it is preferable that the mole ratio of the transition metal organometallic compound and the organometallic compound per metal atom is as follows:

(metal of transition metal organometallic
compound): the organometallic
compound)=100:1 to 1:1000000

More preferably, the ratio is ranged from 1:1 to 100000. Also the ratio of the transition metal organometallic compound and the ionized ionic compound is not limited particularly. However, it is preferable that the mole ratio of the transition metal organometallic compound and the ionized ionic compound is as follows:

(transition metal organometallic compound):
(ionized ionic compound) = 10:1 to 1:1000.

More preferably, the ratio is ranged from 1:1 to 1:100.

The polymerization of olefin by using the catalyst composed of the foregoing components may utilize the organic metal compound as the co-catalyst to meet the desire. For example, when bis(2,3,4,5-tetramethyl phosphoryl) zirconium dichloride-tricarbonyl iron as expressed by general formula (4) is used as the transition metal organometallic compound to synthesize polymers exhibiting different molecular weight distribution, methyl aluminoxane is used as the co-catalyst. When a polymer having a high molecular weight is synthesized, the ionized ionic compound and the organic aluminum compound are used as the co-catalysts. In the foregoing examples, various polymers can be efficiently synthesized. In another example in which bis(2,3,4,5-tetramethylphosphoryl) zirconium dichloride as expressed by general formula (1), the organic aluminum compound and the ionized ionic compound are used, ultra-high-molecular-weight polyethylene can be synthesized. However, the present invention is not limited to the foregoing description.

The polymerization according to the present invention can be performed in the liquid phase and the gas phase. When the polymerization is performed in the liquid phase, any ordinary organic solvent may be employed as the solvent. Specifically, the organic solvent is exemplified by benzene, toluene, xylene, pentane, hexane, heptane, and methylene chloride. Further, olefin such as propylene, 1-butene, 1-hexene 4-methyl-1-pentene, 1-octene may be used as the solvent.

The olefin for use in the polymerization, reaction is exemplified by α-olefin such as ethylene, propylene, 1-butene, 4-methyl-1-pentene, 1-hexene, and styrene, conjugate and non-conjugate diene such as butadiene or 1,4-hexadiene, and cyclic olefin such as cyclobutene. Two or more foregoing mixture components may be polymerized.

The temperature and the time for which the polymerization is performed and the concentration of the catalyst are not limited particularly. It is preferably that the temperature, at which the polymerization is performed, is in a range from −100° C. to 230° C.

EXAMPLES

Examples of the present invention will now be described in detail. The present invention is not limited to the examples.

Reactions were performed under an inert gas atmosphere without exception, and all of solvents used in the reactions were obtained by known methods in which they had been refined dried and deoxidized.

The molecular weight of polyolefin obtained from the present invention was measured by a gel permeation chromatography (GPC) ("150C" manufactured by Waters) under conditions that the column was TSK-gel GMH, the quantity of each sample was 350 μl, the temperature of the column was 140° C., and the flow was 1 ml/minute.

The transition metal organometallic compounds were identified by using $1_{H-NMR}$ (a NMR measuring apparatus "GPX-400" manufactured by Nihon Bunko and solvent $CDCL_3$ was used) and a mass analyzer ("LC/GC/Ms-QP-1000S manufactured by Shimazu adapted to a direct sample introduction method) or an element analyzer.

Preparation

Synthesis of 1-phenyl-2,3,4,5-tetramethylphosphole 17.44 g of 2-butyene was dissolved in 250 ml of dichloromethane, followed by adding to a suspension in which 22.7 g of aluminum chloride was suspended in 250 ml of dichloromethane and which had been cooled to −10° C. A reaction mixture thus obtained was heated to complete reactions.

The reaction mixture was again cooled, and then a solution, in which 31.7 g of dichlorophenyl phosphine was dissolved in 250 ml of dichloromethane, was added. Then, 39 ml of n-butyl phosphine dissolved in 350 ml of dichloromethane was added so that reactions were completed. Then, a post-process was performed, and the pressure was reduced and reaction product was distilled, so that 24 g of desired product was obtained.

Synthesis of bis(2,3,4,5-tetramethylphosphoryle) zirconium dichloride 2.27 g of 1-phenyl-2,3,4,5-tetramethylphosphol was added to 50 ml of tetrahydrofuran, followed by further adding 0.47 g of lithium to react them, so that an excess of lithium was removed. Then, aluminum chloride was added to the reaction solution, followed by neutralize phenyl lithium generated due to the reaction. Then, 1.17 g of zirconium chloride suspended in 10 ml of toluene was added. 2.3 g of orange solid body (desired material) was obtained from the reaction solution.

Synthesis of bis(2,3,4,5-tetramethylphosphoryl) zirconium dichloride-tricarbonyl iron 0.44 g of the foregoing orange solid body and 0.46 g of $Fe_2(CO)_9$ were stirred in methylcyclohexane, followed by heating and refluxing. As a result, 0.1 g of red powder (desired material) was obtained from the reaction solution.

Example 1

500 ml of toluene was introduced into a 2 l-autoclave, followed by adding 1.25 mmol, which was converted into aluminum atoms, of methyl aluminoxane (manufactured by Toso Aquzo and having a molecular weight of 1121) and 1.1 mg of the foregoing bis(2,3,4,5-tetramethylphosphoryl) zirconium dichloride. While supplying ethylene to the autoclave to make the pressure of ethylene to be 8 kg/cm²G, polymerization was performed at 60° C. for one hour. As a result, 72.5 g of granular polyethylene was obtained, the weight average molecular weight (Mw) of which was 490000, and the molecular weight distribution (Mw/number average molecular weight (Mn)) of which was 3.3.

Example 2

Polymerization of ethylene was performed similarly to Example 1 except for using 5 mmol of methyl aluminoxane. As a result, 89.9 g of powder polyethylene was obtained, the Mw of which was 220000 and Mw/Mn of which was 4.3.

Example 3

Polymerization of ethylene was performed similarly to Example 1 except for using 2.2 mg of bis(2,3,4,5-tetramethylphosphoryl) zirconium dichloride and setting the polymerization duration to be 30 minutes. As a result, 65 g of powder polyethylene was obtained, the Mw of which was 290000 and Mw/Mn of which was 4.9.

Example 4

Polymerization of ethylene was performed similarly to Example 1 except for using 0.25 mmol of methyl aluminoxane. As a result, 27.1 g of powder polyethylene was obtained. Polyethylene thus obtained could not be measured by the GPC because of an assumption that the molecular weight of the polyethylene was too high.

Example 5

Polymerization of ethylene was performed similarly to Example 1 except for using 25 mmol of methyl aluminoxane. As a result, 93.2 g of powder polyethylene was obtained, the Mw of which was 48800 and Mw/Mn of which was 4.05.

Example 6

500 ml of toluene was introduced into a 2 l-autoclave, followed by adding 1.25 mmol, which was converted into aluminum atoms, of methyl aluminoxane (manufactured by Toso Aquzo and having a molecular weight of 1121) and 1.1 mg of the foregoing bis(2,3,4,5-tetramethylphosphoryl) zirconium dichloride. 500 ml of propylene was added to the autoclave, and then the temperature was raised to 60° C., so that polymerization was performed for one hour. As a result, 3.1 g of polypropylene was obtained.

Example 7

500 ml of toluene was introduced into a 2 l-autoclave, followed by adding 0.25 mmol of triisobutyl aluminum and 1.1 mg of the foregoing bis(2,3,4,5-tetramethylphosphoryl) zirconium dichloride. Then, a 10 ml of toluene solution containing 10 mg of anilinium tetrakispentafluorophenyl borate was added to the autoclave. The solution was stirred for several minutes, and then polymerization was performed at 60° C. for one hour while supplying ethylene to the autoclave to make the pressure of ethylene to be 8 kg/cm$^2$G. As a result, 22.6 g of granular polyethylene (the melting point of which was 137° C. and the weight average molecular weight (Mw) of which was 640000) was obtained.

Example 8

Polymerization of ethylene was performed similarly to Example 7 except for using 11 mg of triphenylcarbonium tetrakispentafluorophenyl borate in place of anilinium tetrakispentafluorophenyl borate. As a result, 33 g of polyethylene was obtained.

Example 9

Polymerization of ethylene was performed similarly to Example 8 except for using trimethyl aluminum in place of triisobutyl aluminum. As a result, 2.7 g of polyethylene was obtained.

Example 10

600 ml of toluene and 200 ml of 1-hexene were introduced into a 5 l-autoclave, followed by adding 0.25 mmol of triisobutyl aluminum and 2.2 mg of the foregoing bis(2,3,4,5-tetramethylphosphoryl) zirconium dichloride. Then, a 10 ml of toluene solution containing 8.1 mg of anilinium tetrakispentafluorophenyl borate was added to the autoclave. The solution was stirred for several minutes, and then polymerization was performed at 60° C. for one hour while supplying ethylene to the autoclave to make the pressure of ethylene to be 8 kg/cm$^2$G. As a result, 63.7 g of powder polymer was obtained.

Example 11

600 ml of toluene and 25 ml of 1-hexene were introduced into a 5 l-autoclave, followed by adding 0.25 mmol of triisobutyl aluminum and 2.2 mg of the foregoing bis(2,3,4,5-tetramethylphosphoryl) zirconium dichloride. Then, a 10 ml of toluene solution containing 8.1 mg of anilinium tetrakispentafluorophenyl borate was added to the autoclave. The solution was stirred for several minutes, and then polymerization was performed at 60° C. for one hour while supplying ethylene to the autoclave to make the pressure of ethylene to be 8 kg/cm$^2$G. As a result, 55.4 g of granular polyethylene (the melting point of which was 129° C. and the weight average molecular weight (Mw) of which was 84000) was obtained.

Example 12

500 ml of toluene was introduced into a 2 l-autoclave, followed by adding 2.5 mmol of triisobutyl aluminum and 1.1 mg of the foregoing bis(2,3,4,5-tetramethylphosphoryl) zirconium dichloride. The solution was stirred for several minutes, and then polymerization was performed at 60° C. for one hour while supplying ethylene to the autoclave to make the pressure of ethylene to be 8 kg/cm$^2$G. As a result, 1.5 g of polyethylene was obtained.

Example 13

500 ml of toluene was introduced into a 2 l-autoclave, followed by adding 25 mmol, which was converted into aluminum atoms, of methyl aluminoxane (manufactured by Toso Aquzo and having a molecular weight of 1121) and 1.4 mg of the foregoing bis(2,3,4,5-tetramethylphosphoryl) zirconium dichloride-tricarbonyl iron. Polymerization was performed at 60° C. for one hour while supplying ethylene to the autoclave to make the pressure of ethylene to be 8 kg/cm$^2$G. As a result, 46 g of polyethylene was obtained (the weight average molecular weight (Mw) of which was 71000, and the molecular weight distribution (Mw/Mn)) of which was 5.6.

Example 14

Polymerization of ethylene was performed similarly to Example 13 except for using 1.25 mmol of methyl aluminoxane. As a result, 14 g of polyethylene was obtained, the Mw of which was 20000 and Mw/Mn of which was 2.5.

Example 15

Polymerization of ethylene was performed similarly to Example 14 except for setting the polymerization temperature to 90° C. As a result, 8 g of polyethylene was obtained, the Mw of which was 230000 and Mw/Mn of which was 11.8.

Example 16

Polymerization of ethylene was performed similarly to Example 14 except for using 1.25 mmol of triisobutyl aluminum in addition to 1.25 mmol of methyl aluminoxane. As a result, 24 g of powder polyethylene was obtained. Polyethylene thus obtained could not be measured by the GPC because of an assumption that the molecular weight of the polyethylene was too high. The molecular weight (Mv) obtained from the viscosity average was 250000.

Example 17

Polymerization of ethylene was performed similarly to Example 13 except for adding 100 ml of 1-hexene. As a result, 23 g of ethylene-hexene copolymer exhibiting uniform composition distribution was obtained. Mw of the obtained ethylene-hexene copolymer was 61000 and Mw/Mn of the same was 4.2.

Example 18

500 ml of toluene was introduced into a 2 l-autoclave, followed by adding 1.25 mmol of trimethyl aluminum and 1.4 mg of the foregoing bis(2,3,4,5-tetramethylphosphoryl) zirconium dichloride-tricarbonyl iron. Polymerization was performed at 60° C. for one hour while supplying ethylene to the autoclave to make the pressure of ethylene to be 8 kg/cm$^2$G. As a result, 0.1 g of polyethylene was obtained.

Example 19

500 ml of toluene was introduced into a 2 l-autoclave, followed by adding 1.25 mmol of triisobutyl aluminum and 1.4 mg of the foregoing bis(2,3,4,5-tetramethylphosphoryl) zirconium dichloride-tricarbonyl iron. Further, 10 mg of anilinium tetrakispentafluorophenyl borate synthesized by a known method and dissolved in 10 ml of toluen was added to the autoclave. Polymerization was performed at 60° C. for 30 minutes while supplying ethylene to the autoclave to make the pressure of ethylene to be 8 kg/cm$^2$G. As a result, 54 g of polyethylene was obtained, Mw of which was 233000 and Mw/Mn of which was 2.0.

Example 20

Synthesis of (cyclopentadienyl) (2,3,4,5-tetramethylphosphoryl) zirconium dichloride 2.33 g of monocyclopentadienyl zirconium trichloride suspended in 50 ml toluene was added to a 50 ml solution of tetrahydrofuran containing 8.88 mmol of lithium salt of 2,3,4,5-tetramethylphosphol. 1.0 g of light-yellow solid body was obtained from the reaction solution by re-crystallization.

The analyzed values of the product were as follows:

|                   | C wt % | H wt % | Cl wt % |
|-------------------|--------|--------|---------|
| Analyzed Values   | 43.46  | 4.78   | 18.8    |
| Calculated Values | 42.62  | 4.68   | 19.4    |

Figure 1:
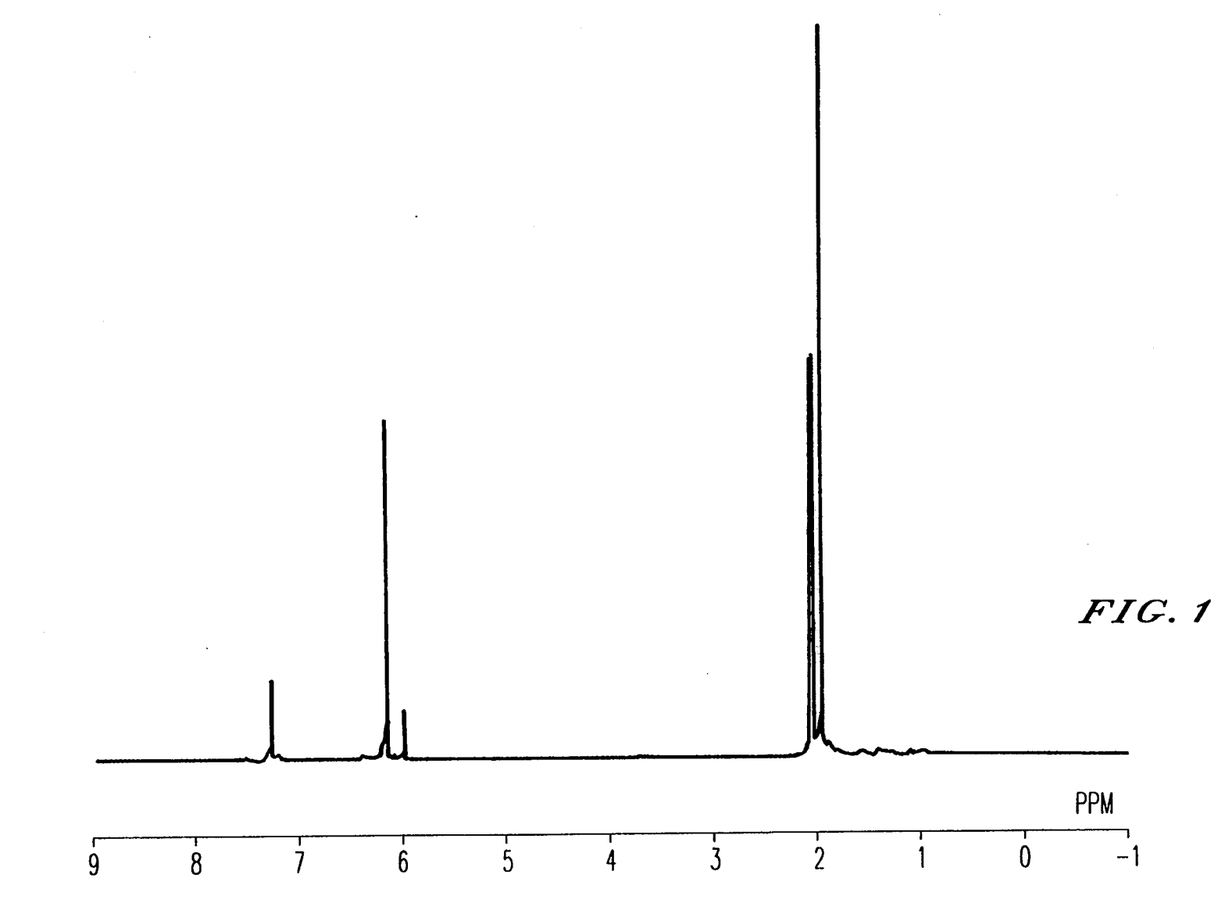
FIG. 1 is IH-NMR spectrum of the compound obtained by Example 20.
Figure 2A:
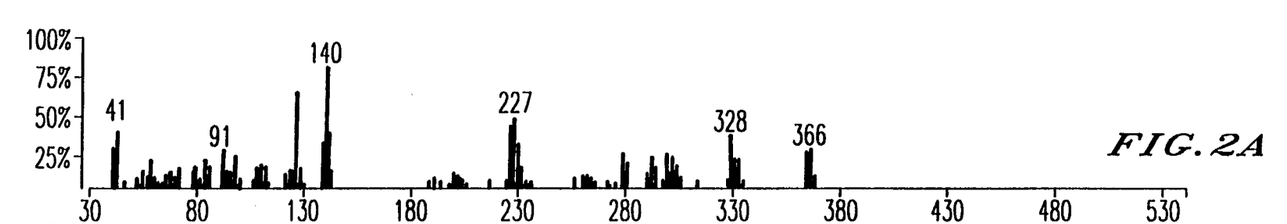
FIG. 2 is Mass spectrum of the compound obtained by Example 20.
Figure 2B:
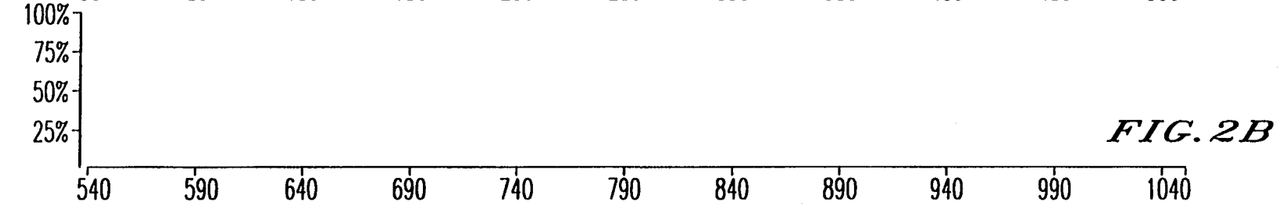

$^1$H-NMR spectrum is shown in FIG. 1, while Mass spectrum is shown in FIG. 2

Example 21

Synthesis of (indenyl) (2,3,4,5-tetramethylphosphoryl) zirconium dichloride 4.68 g of monoindenyl zirconium trichloride suspended in 100 ml toluene was added to a 50 ml solution of tetrahydrofuran containing 11 mmol of lithium salt of 2,3,4,5-tetramethylphosphol. 1.48 g of light-yellow solid body was obtained from the reaction solution by re-crystallization.

|                   | C wt % | H wt % | Cl wt % |
|-------------------|--------|--------|---------|
| Analyzed Values   | 48.88  | 4.98   | 16.3    |
| Calculated Values | 49.03  | 4.60   | 17.0    |

Figure 3:
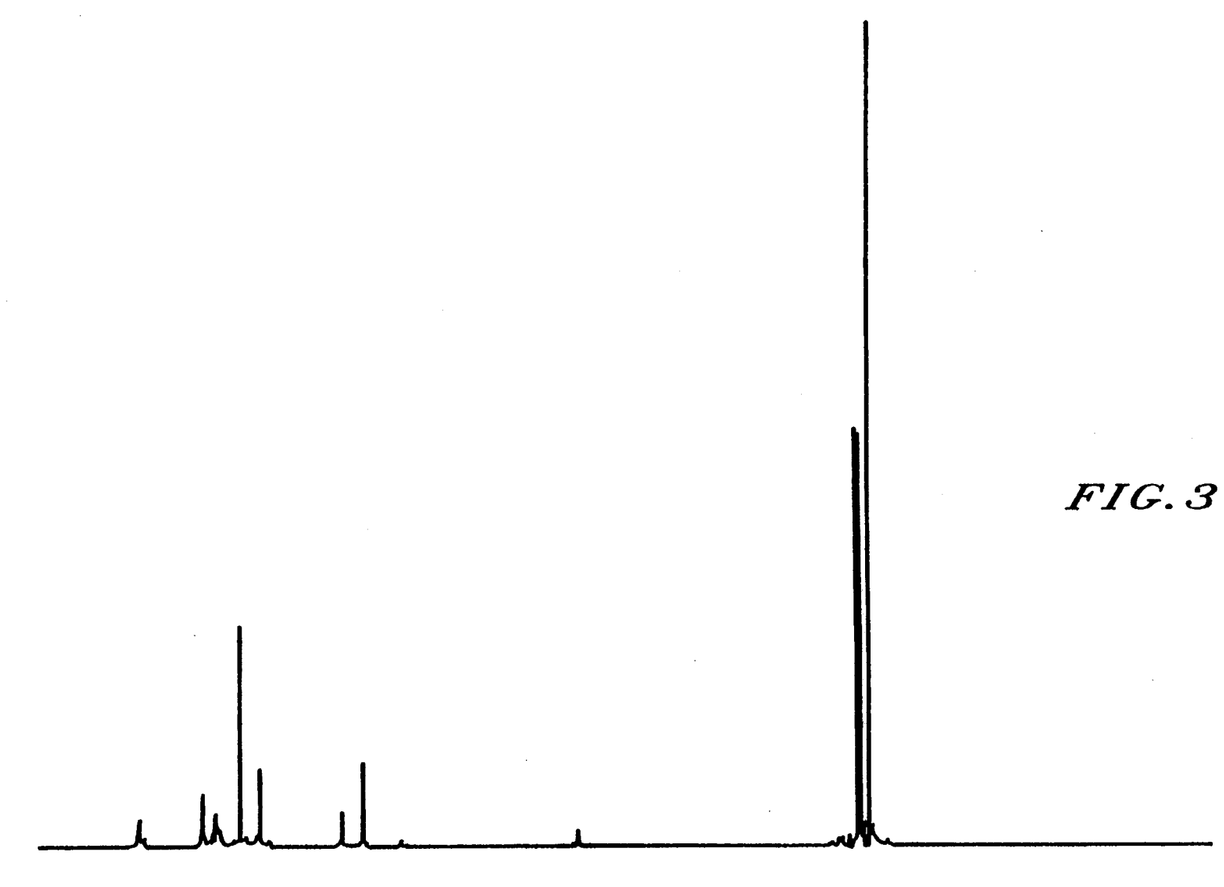
FIG. 3 is IH-NMR spectrum of the compound obtained by Example 21.
Figure 4A:
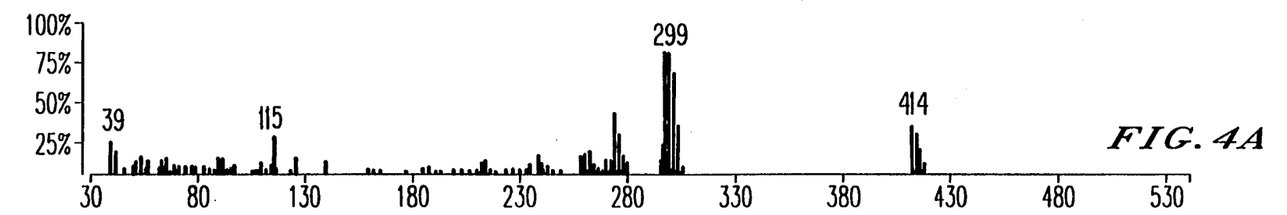
FIG. 4 is Mass spectrum of the compound obtained by Example 21.
Figure 4B:
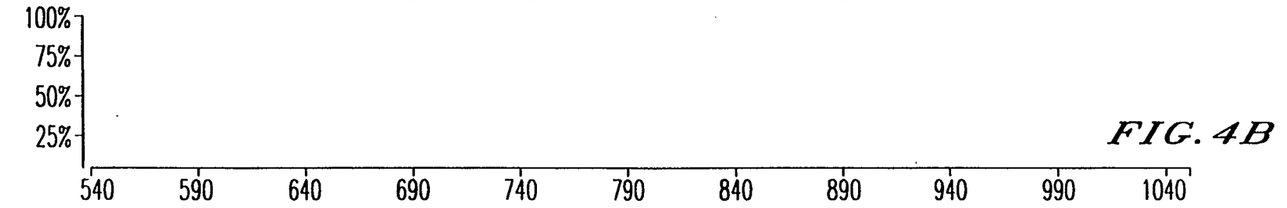

$^1$H-NMR spectrum is shown in FIG. 3, while Mass spectrum is shown in FIG. 4.

Example 22

Synthesis of bis(2,3,4,5-tetramethylphosphoryl) titanium dichloride 2.6 g of titanium chloride tetrahydrofuran complex suspended in 50 ml toluene was added to a 50 ml solution of tetrahydrofuran containing 15.9 mmol of lithium salt of 2,3,4,5-tetramethylphosphol. 2.5 g of orange oily solid body was obtained from the reaction solution (the obtained compound contained a small quantity of phenyl aluminum compound).

Figure 5:
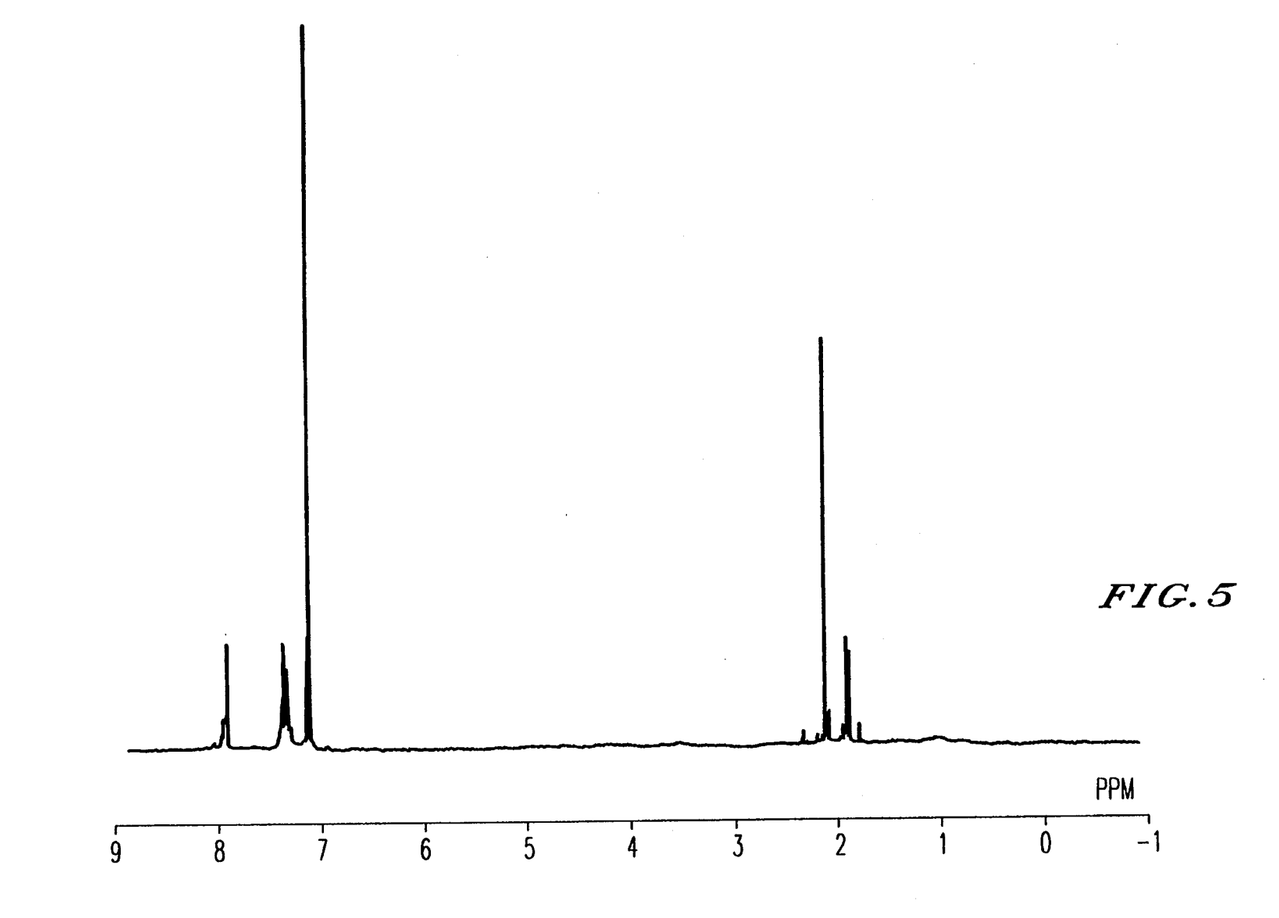
FIG. 5 is IH-NMR spectrum of the compound obtained by Example 22.

$^1$H-NMR spectrum is shown in FIG. 5.

Example 23

500 ml of toluene and 15 ml of 1-hexene were introduced into a 2 l-autoclave, followed by adding 5 mmol, which was converted into aluminum atoms, of methyl aluminoxane (manufactured by Toso Aquzo and having a molecular weight of 1121) and 0.2 mg of the foregoing (cyclopentadienyl) (2,3,4,5-tetramethylphosphoryl) zirconium dichloride. Hydrogen was introduced into the autoclave to make the pressure to be 0.5 kg/cm$^2$, and then polymerization was performed at 60° C. for 20 minutes while supplying ethylene to the autoclave to make the total pressure to be 8 kg/cm$^2$G. As a result, 28.6 g of granular polyethylene was obtained, the weight average molecular weight (Mw) of which was 17100, and the molecular weight distribution (Mw/Mn)) of which was 2.8.

Example 24

Polymerization was performed similarly to Example 23 except for making the quantity of 1-hexene to be 25 ml and for adding no hydrogen. As a result, 16.9 g of polyethylene was obtained.

Example 25

500 ml of toluene was introduced into a 2 l-autoclave, followed by adding 0.25 mmol of triisobutyl aluminum and 0.2 mg of the foregoing (cyclopentadienyl) (2,3,4,5-tetramethylphosphoryl) zirconium dichloride. Further, 2 mg of anilinium tetrakispentafluorophenyl borate synthesized by a known method and dissolved in 10 ml of toluen was added to the autoclave. Polymerization was performed at 60° C. for 60 minutes while supplying ethylene to the autoclave to make the pressure of ethylene to be 8 kg/cm$^2$G. As a result, 22.3 g of polyethylene was obtained.

Example 26

Polymerization was performed similarly to Example 25 except for adding 25 ml of 1-hexene and for setting the polymerization duration to 20 minutes. As a result, 22.4 g of polyethylene was obtained (the reciting point of which was 127.1° C.).

According to the present invention, sole use of the transition metal organometallic compound comprising cyclic compounds including heteroatoms and π-electrons as the ligand and the organometallic compound and/or ionized ionic compound or use of the same in such a manner that they are combined to co-exist so that polyolefin exhibiting excellent physical properties and processability can be obtained in terms of polymerization activity with respect to olefin, excellent appearance of obtained polymer, wide molecular weight distribution and satisfactory composition at the time of the copolymerization. Consequently, the present invention can be utilized to manufacture the catalyst for polymerization and as the method of polymerizing olefin that exhibits excellent industrial value.

What is claimed is:

1. A catalyst for polymerizing olefin, comprising a transition metal organometallic compound and an organometallic compound as components thereof, wherein said transition metal organometallic compound comprises a transition metal in any one of group 3 to group 10 of the periodic table and cyclic compounds containing a heteroatom in group 15 of the periodic table and having a cyclic structure including a π-bonded portion and composed of said heteroatom and said π-bonded portion, wherein said transition metal has a bond of a π-bonding heterocyclic ligand, said heteroatom and said π-bonded portion, and said organometallic compound comprises a metal selected from the group consisting of metals of groups 1, 2, 12 and 13 of the periodic table.

2. A catalyst for polymerizing olefin according to claim 1, wherein said organometallic compound is an organic aluminum compound.

3. A catalyst for polymerizing olefin according to claim 1, wherein said organometallic compound is aluminoxane expressed by the following general formula (6) or (7):

(6)

(7)

where $R^{10}$ may be the same or different from one another, $R^{10}$ being hydrogen, halogen, alkoxide, an alkyl group, an aryl group or a aralkyl group, and q is an integer from 0 to 100.

4. A catalyst for polymerizing olefin according to claim 3, wherein an organometallic compound except for aluminoxane is contained as said organometallic compound.

5. A catalyst for polymerizing olefin according to any one of claims 1 to 4, wherein an ionized ionic compound expressed by the following general formula (8) is contained as a component:

$$[C^+][A^-] \qquad (8)$$

where $[C^+]$ is cation, and $[A^-]$ is anion.

* * * * *